United States Patent
Ludwin et al.

(10) Patent No.: US 8,731,859 B2
(45) Date of Patent: May 20, 2014

(54) CALIBRATION SYSTEM FOR A FORCE-SENSING CATHETER

(75) Inventors: Doron Ludwin, Haifa (IL); Yevgeny Bonyak, Haifa (IL); Dror Shlomo Levy, Qiryat Tivon (IL)

(73) Assignee: Biosense Webster (Israel) Ltd. (IL)

( * ) Notice: Subject to any disclaimer, the term of this patent is extended or adjusted under 35 U.S.C. 154(b) by 560 days.

(21) Appl. No.: 12/899,909

(22) Filed: Oct. 7, 2010

(65) Prior Publication Data

US 2012/0089358 A1  Apr. 12, 2012

(51) Int. Cl.
G01C 19/00 (2013.01)
A61B 5/04 (2006.01)
A61F 13/20 (2006.01)

(52) U.S. Cl.
USPC .............................. 702/104; 600/372; 604/14

(58) Field of Classification Search
USPC ......... 702/104, 33, 35–36, 41–43, 81, 84–85, 702/98, 105, 127, 138–140, 182–183, 185, 702/189; 600/372–374, 377, 433, 435, 459, 600/462, 466, 585; 604/11, 14, 19, 22, 27, 604/36, 73, 508; 606/1, 32, 41, 129, 201; 73/1.79, 760, 763, 768, 774; 29/592.1, 29/593
See application file for complete search history.

(56) References Cited

U.S. PATENT DOCUMENTS

| | | | |
|---|---|---|---|
| 3,841,150 A | 10/1974 | Pearson | |
| 3,971,364 A | 7/1976 | Fletcher et al. | |
| 4,764,114 A | 8/1988 | Jeffcoat et al. | |
| 4,856,993 A | 8/1989 | Maness et al. | |
| 4,930,494 A | 6/1990 | Takehana et al. | |
| 5,263,493 A | 11/1993 | Avitall | |
| 5,368,564 A | 11/1994 | Savage | |
| 5,391,199 A | 2/1995 | Ben-Haim | |
| 5,462,527 A | 10/1995 | Stevens-Wright et al. | |
| 5,487,757 A | 1/1996 | Truckai et al. | |
| 5,499,542 A | 3/1996 | Morlan | |
| 5,542,434 A | 8/1996 | Imran et al. | |

(Continued)

FOREIGN PATENT DOCUMENTS

| | | |
|---|---|---|
| DE | 19750441 C2 | 6/1999 |
| EP | 928601 A1 | 7/1999 |

(Continued)

OTHER PUBLICATIONS

Guo et al., Control and Experimental Results of a Catheter Operating System, Feb. 21-26, 2009, Proceedings of the 2008 IEEE, International Conference on Robotics and Biomimetics, Bankok, Thailand, pp. 91-95.*

(Continued)

Primary Examiner — Toan Le

(57) ABSTRACT

An apparatus, consisting of a rolling element, which is resting on a surface, and a force-sensing device, which is coupled to the surface. The force-sensing device is configured to make a first measurement indicative of a force exerted in a direction perpendicular to the surface. The force is exerted by a force-sensing probe pressing against the rolling element so as to hold the rolling element stationary. The apparatus further includes a calibration processor, which is configured to collect the first measurement from the sensing device, to collect a second measurement indicative of the force from the force-sensing probe, and to calibrate the force-sensing probe based on the first and second measurements.

26 Claims, 3 Drawing Sheets

(56) References Cited

U.S. PATENT DOCUMENTS

| | | |
|---|---|---|
| 5,558,091 A | 9/1996 | Acker et al. |
| 5,563,354 A | 10/1996 | Kropp |
| 5,662,124 A | 9/1997 | Wilk |
| 5,673,695 A | 10/1997 | McGee et al. |
| 5,680,860 A | 10/1997 | Imran |
| 5,685,878 A | 11/1997 | Falwell et al. |
| 5,728,149 A | 3/1998 | Laske et al. |
| 5,769,843 A | 6/1998 | Abela et al. |
| 5,826,576 A | 10/1998 | West |
| 5,833,608 A | 11/1998 | Acker |
| 5,836,894 A | 11/1998 | Sarvazyan |
| 5,860,974 A | 1/1999 | Abele |
| 5,861,024 A | 1/1999 | Rashidi |
| 5,902,248 A | 5/1999 | Millar et al. |
| 5,916,147 A | 6/1999 | Boury |
| 5,944,022 A | 8/1999 | Nardella et al. |
| 5,947,320 A | 9/1999 | Bordner et al. |
| 5,964,757 A | 10/1999 | Ponzi |
| 5,974,320 A | 10/1999 | Ward et al. |
| 5,983,126 A | 11/1999 | Wittkampf |
| 6,048,329 A | 4/2000 | Thompson et al. |
| 6,063,022 A | 5/2000 | Ben-Haim |
| 6,123,699 A | 9/2000 | Webster, Jr. |
| 6,171,277 B1 | 1/2001 | Ponzi |
| 6,177,792 B1 | 1/2001 | Govari et al. |
| 6,183,463 B1 | 2/2001 | Webster, Jr. |
| 6,198,974 B1 | 3/2001 | Webster, Jr. |
| 6,201,387 B1 | 3/2001 | Govari |
| 6,203,493 B1 | 3/2001 | Ben-Haim |
| 6,216,027 B1 | 4/2001 | Willis et al. |
| 6,226,542 B1 | 5/2001 | Reisfeld |
| 6,239,724 B1 | 5/2001 | Doron et al. |
| 6,241,724 B1 | 6/2001 | Fleischman et al. |
| 6,266,551 B1 * | 7/2001 | Osadchy et al. ............... 600/424 |
| 6,272,371 B1 | 8/2001 | Shlomo |
| 6,272,672 B1 | 8/2001 | Conway |
| 6,301,496 B1 | 10/2001 | Reisfeld |
| 6,332,089 B1 | 12/2001 | Acker et al. |
| 6,334,837 B1 | 1/2002 | Hein |
| 6,335,617 B1 | 1/2002 | Osadchy et al. |
| 6,351,549 B1 | 2/2002 | Souluer |
| 6,436,059 B1 | 8/2002 | Zanelli |
| 6,456,864 B1 | 9/2002 | Swanson et al. |
| 6,484,118 B1 | 11/2002 | Govari |
| 6,551,302 B1 | 4/2003 | Rosinko et al. |
| 6,569,098 B2 | 5/2003 | Kawchuk |
| 6,574,492 B1 | 6/2003 | Ben-Haim et al. |
| 6,584,856 B1 | 7/2003 | Biter et al. |
| 6,602,242 B1 | 8/2003 | Fung et al. |
| 6,612,992 B1 | 9/2003 | Hossack et al. |
| 6,618,612 B1 | 9/2003 | Acker et al. |
| 6,690,963 B2 | 2/2004 | Ben-Haim et al. |
| 6,695,808 B2 | 2/2004 | Tom |
| 6,711,429 B1 | 3/2004 | Gilboa et al. |
| 6,727,371 B2 | 4/2004 | Müller et al. |
| 6,814,733 B2 | 11/2004 | Schwartz et al. |
| 6,835,173 B2 | 12/2004 | Couvillon, Jr. |
| 6,892,091 B1 | 5/2005 | Ben-Haim et al. |
| 6,915,149 B2 | 7/2005 | Ben-Haim |
| 6,945,956 B2 | 9/2005 | Waldhauser et al. |
| 6,964,205 B2 | 11/2005 | Papakostas et al. |
| 6,973,339 B2 | 12/2005 | Govari |
| 6,997,924 B2 | 2/2006 | Schwartz et al. |
| 7,077,823 B2 | 7/2006 | McDaniel |
| 7,156,816 B2 | 1/2007 | Schwartz et al. |
| 7,235,070 B2 | 6/2007 | Vanney |
| 7,297,116 B2 | 11/2007 | Varghese et al. |
| 7,306,593 B2 | 12/2007 | Keidar et al. |
| 7,306,599 B2 | 12/2007 | Karasawa et al. |
| 7,311,704 B2 | 12/2007 | Paul et al. |
| 7,397,364 B2 | 7/2008 | Govari |
| 7,435,232 B2 | 10/2008 | Liebschner |
| 7,465,288 B2 | 12/2008 | Dudney et al. |
| 7,481,774 B2 | 1/2009 | Brockway et al. |
| 7,536,218 B2 | 5/2009 | Govari et al. |
| 7,604,605 B2 | 10/2009 | Zvuloni |
| 7,662,151 B2 | 2/2010 | Crompton, Jr. et al. |
| 7,681,432 B2 | 3/2010 | Hay et al. |
| 7,686,767 B2 | 3/2010 | Maschke |
| 7,914,440 B2 | 3/2011 | Otawara |
| 7,959,601 B2 | 6/2011 | McDaniel et al. |
| 7,984,659 B2 | 7/2011 | Fujimoto et al. |
| 8,043,216 B2 | 10/2011 | Matsumura |
| 8,046,049 B2 | 10/2011 | Govari et al. |
| 8,083,691 B2 | 12/2011 | Goldenberg et al. |
| 8,137,275 B2 | 3/2012 | Fan et al. |
| 8,374,819 B2 | 2/2013 | Govari et al. |
| 2001/0047129 A1 | 11/2001 | Hall et al. |
| 2001/0047133 A1 | 11/2001 | Gilboa et al. |
| 2002/0002329 A1 | 1/2002 | Avitall |
| 2002/0065455 A1 | 5/2002 | Ben-Haim et al. |
| 2002/0068866 A1 | 6/2002 | Zikorus et al. |
| 2002/0068931 A1 | 6/2002 | Wong et al. |
| 2002/0165461 A1 | 11/2002 | Hayzelden et al. |
| 2002/0193781 A1 | 12/2002 | Loeb |
| 2003/0120150 A1 | 6/2003 | Govari |
| 2003/0120195 A1 | 6/2003 | Milo et al. |
| 2003/0130615 A1 | 7/2003 | Tom |
| 2003/0158494 A1 | 8/2003 | Dahl et al. |
| 2003/0187389 A1 | 10/2003 | Morency et al. |
| 2004/0049255 A1 | 3/2004 | Jain et al. |
| 2004/0064024 A1 | 4/2004 | Sommer |
| 2004/0068178 A1 | 4/2004 | Govari |
| 2004/0097806 A1 | 5/2004 | Hunter et al. |
| 2004/0102769 A1 | 5/2004 | Schwartz et al. |
| 2004/0147920 A1 | 7/2004 | Keidar |
| 2004/0244464 A1 | 12/2004 | Hajdukiewicz et al. |
| 2004/0254458 A1 | 12/2004 | Govari |
| 2005/0033135 A1 | 2/2005 | Govari |
| 2005/0080429 A1 | 4/2005 | Freyman et al. |
| 2005/0096590 A1 | 5/2005 | Gullickson et al. |
| 2005/0228274 A1 | 10/2005 | Boese et al. |
| 2005/0277875 A1 | 12/2005 | Selkee |
| 2006/0009690 A1 | 1/2006 | Fuimaono et al. |
| 2006/0009735 A1 | 1/2006 | Viswanathan et al. |
| 2006/0015096 A1 | 1/2006 | Hauck et al. |
| 2006/0064038 A1 | 3/2006 | Omata et al. |
| 2006/0074297 A1 | 4/2006 | Viswanathan |
| 2006/0173480 A1 | 8/2006 | Zhang |
| 2006/0184106 A1 | 8/2006 | McDaniel et al. |
| 2006/0200049 A1 | 9/2006 | Leo et al. |
| 2006/0247618 A1 | 11/2006 | Kaplan et al. |
| 2007/0021742 A1 | 1/2007 | Viswanathan |
| 2007/0060832 A1 | 3/2007 | Levin |
| 2007/0060847 A1 | 3/2007 | Leo et al. |
| 2007/0100332 A1 | 5/2007 | Paul et al. |
| 2007/0106114 A1 | 5/2007 | Sugimoto et al. |
| 2007/0142749 A1 | 6/2007 | Khatib et al. |
| 2007/0151391 A1 | 7/2007 | Larkin et al. |
| 2007/0156114 A1 | 7/2007 | Pappone |
| 2007/0161882 A1 | 7/2007 | Pappone |
| 2007/0167740 A1 | 7/2007 | Grunewald et al. |
| 2007/0167818 A1 | 7/2007 | Osborn et al. |
| 2007/0179492 A1 | 8/2007 | Pappone |
| 2007/0185397 A1 | 8/2007 | McGee et al. |
| 2007/0191829 A1 | 8/2007 | Wallace et al. |
| 2007/0197927 A1 | 8/2007 | Ofek |
| 2007/0197939 A1 | 8/2007 | Wallace et al. |
| 2007/0282211 A1 | 12/2007 | Aeby et al. |
| 2008/0009750 A1 | 1/2008 | Aeby et al. |
| 2008/0015568 A1 | 1/2008 | Paul et al. |
| 2008/0051704 A1 | 2/2008 | Patel et al. |
| 2008/0065111 A1 | 3/2008 | Blumenkranz et al. |
| 2008/0071267 A1 | 3/2008 | Wang et al. |
| 2008/0077049 A1 | 3/2008 | Hirshman |
| 2008/0146918 A1 | 6/2008 | Magnin et al. |
| 2008/0183075 A1 | 7/2008 | Govari et al. |
| 2008/0200843 A1 | 8/2008 | Williams et al. |
| 2008/0249467 A1 | 10/2008 | Burnett et al. |
| 2008/0249522 A1 | 10/2008 | Pappone et al. |
| 2008/0255540 A1 | 10/2008 | Selkee |
| 2008/0269606 A1 | 10/2008 | Matsumura |
| 2008/0275428 A1 | 11/2008 | Tegg et al. |
| 2008/0275442 A1 | 11/2008 | Paul et al. |

(56) References Cited

U.S. PATENT DOCUMENTS

| | | |
|---|---|---|
| 2008/0275465 A1 | 11/2008 | Paul et al. |
| 2008/0281319 A1 | 11/2008 | Paul et al. |
| 2008/0287777 A1 | 11/2008 | Li et al. |
| 2008/0288038 A1 | 11/2008 | Paul et al. |
| 2008/0294144 A1 | 11/2008 | Leo |
| 2008/0294158 A1 | 11/2008 | Pappone et al. |
| 2009/0010021 A1 | 1/2009 | Smith et al. |
| 2009/0093806 A1 | 4/2009 | Govari et al. |
| 2009/0138007 A1 | 5/2009 | Govari et al. |
| 2009/0158511 A1 | 6/2009 | Maze et al. |
| 2009/0177111 A1 | 7/2009 | Miller et al. |
| 2009/0275966 A1 | 11/2009 | Mitusina |
| 2009/0287118 A1 | 11/2009 | Malek |
| 2009/0294361 A1 | 12/2009 | Larsen |
| 2009/0306515 A1 | 12/2009 | Matsumura et al. |
| 2009/0306650 A1 | 12/2009 | Govari et al. |
| 2010/0063478 A1 | 3/2010 | Selkee |
| 2010/0069921 A1 | 3/2010 | Miller et al. |
| 2010/0121138 A1 | 5/2010 | Goldenberg et al. |
| 2010/0137845 A1 | 6/2010 | Ramstein et al. |
| 2010/0152574 A1 | 6/2010 | Erdman |
| 2010/0160770 A1 | 6/2010 | Govari et al. |
| 2010/0160778 A1 | 6/2010 | Eskandari et al. |
| 2010/0168620 A1 | 7/2010 | Klimovitch et al. |
| 2010/0168918 A1 | 7/2010 | Zhao et al. |
| 2010/0292566 A1 | 11/2010 | Nagano et al. |
| 2010/0298826 A1 | 11/2010 | Leo et al. |
| 2011/0054354 A1 | 3/2011 | Hunter et al. |
| 2011/0054355 A1 | 3/2011 | Hunter et al. |
| 2011/0071436 A1 | 3/2011 | Althoefer et al. |
| 2011/0130648 A1 | 6/2011 | Beeckler et al. |
| 2011/0153252 A1 | 6/2011 | Govari et al. |
| 2011/0153253 A1* | 6/2011 | Govari et al. ............... 702/98 |
| 2011/0160556 A1 | 6/2011 | Govari |
| 2011/0172538 A1 | 7/2011 | Sumi |
| 2011/0184406 A1 | 7/2011 | Selkee |
| 2011/0307207 A1 | 12/2011 | Govari et al. |
| 2012/0004576 A1 | 1/2012 | Govari et al. |
| 2012/0041295 A1 | 2/2012 | Schultz |
| 2012/0089358 A1 | 4/2012 | Ludwin et al. |
| 2012/0108988 A1 | 5/2012 | Ludwin et al. |
| 2012/0149966 A1 | 6/2012 | Ludwin et al. |
| 2012/0149967 A1 | 6/2012 | Ludwin et al. |
| 2012/0150075 A1 | 6/2012 | Ludwin et al. |
| 2012/0184864 A1 | 7/2012 | Harlev et al. |
| 2012/0184865 A1 | 7/2012 | Harlev et al. |
| 2012/0253167 A1 | 10/2012 | Bonyak et al. |
| 2012/0259194 A1 | 10/2012 | Selkee |
| 2012/0271145 A1 | 10/2012 | Govari et al. |
| 2012/0310116 A1 | 12/2012 | Ludwin et al. |
| 2012/0316407 A1 | 12/2012 | Anthony et al. |
| 2013/0018306 A1 | 1/2013 | Ludwin |

FOREIGN PATENT DOCUMENTS

| | | |
|---|---|---|
| EP | 980693 A1 | 2/2000 |
| EP | 1502555 A1 | 2/2005 |
| EP | 1586281 A1 | 10/2005 |
| EP | 1690564 A1 | 8/2006 |
| EP | 1743575 A2 | 1/2007 |
| EP | 1820464 A1 | 8/2007 |
| EP | 1897581 A2 | 3/2008 |
| EP | 2000789 A2 | 12/2008 |
| EP | 2047797 A2 | 4/2009 |
| EP | 2127604 A1 | 12/2009 |
| EP | 2130508 B1 | 12/2009 |
| EP | 2196143 A1 | 6/2010 |
| EP | 2305115 A1 | 4/2011 |
| EP | 2338411 A1 | 6/2011 |
| EP | 2338412 A1 | 6/2011 |
| EP | 2172240 B1 | 12/2012 |
| JP | 8243168 A | 9/1996 |
| JP | 2000126301 A | 5/2000 |
| JP | 2000508224 A | 7/2000 |
| JP | 2005040215 | 2/2005 |
| JP | 2005237964 A | 9/2005 |
| JP | 2005/345215 | 12/2005 |
| JP | 2006064465 A | 3/2006 |
| JP | 2006255401 A | 9/2006 |
| JP | 2007181696 A | 7/2007 |
| WO | 94/17856 A1 | 8/1994 |
| WO | 95/10326 A | 4/1995 |
| WO | WO 96/05768 A1 | 2/1996 |
| WO | 97/29709 A | 8/1997 |
| WO | 97/29710 A | 8/1997 |
| WO | WO 97/29678 A2 | 8/1997 |
| WO | 98/29032 A | 7/1998 |
| WO | 03/020139 A | 3/2003 |
| WO | 2006/086152 A | 8/2006 |
| WO | 2006/092563 A | 9/2006 |
| WO | 2006/135483 A2 | 12/2006 |
| WO | 2007/015139 A2 | 2/2007 |
| WO | 2007/025230 A | 3/2007 |
| WO | 2007/050960 A | 5/2007 |
| WO | 2007/067938 A | 6/2007 |
| WO | 2007/076312 A2 | 7/2007 |
| WO | 2007/082216 A | 7/2007 |
| WO | WO 2007/098494 A1 | 8/2007 |
| WO | 2007/111182 A | 10/2007 |
| WO | 2008/053402 A1 | 5/2008 |
| WO | 2008/147599 A1 | 12/2008 |
| WO | 2009/065140 A1 | 5/2009 |
| WO | 2009/078280 A | 6/2009 |
| WO | 2009/085470 A | 7/2009 |
| WO | WO 2009/147399 A1 | 12/2009 |
| WO | 2010/008975 A | 1/2010 |
| WO | 2011/046874 A1 | 4/2011 |

OTHER PUBLICATIONS

EP Search Report Appln No. 11182854.7-2310 dated Feb. 3, 2012.
European Search Report, dated Sep. 15, 2011, for European Pat. Appln. No. 11169251.
European Search Report, dated Mar. 28, 2011, for European Pat. Appln. No. 10252191.1.
Instron Marketing Brochure, "Medical Device Testing Systems", Instron 2007 http://web.archive.org/web/20080318092822/http://www.instron.com.tr/wa/library/streamfile.aspx?doc=1678&download=true.
Instron, "Series 3300 Load Frames, Reference Manual Equipment", Instron, pp. 1-5 and 1-10, 2004.
Peirs, J. et al., "Design of an Optical Force Sensor for Force Feedback During Minimally Invasive Robotic Surgery", Eurosensors XVII, 2003, http://www.mech.kuleuven.be/micro/pub/medic/Paper_Eurosensors_2003_MIS_sensor_extended.pdf.
Biter, William J. et al., "Magnetic Wire Strain Sensor", 33rd International Sampe Technical Conference, Nov. 5-8, 2001, vol. 33, pp. 12-23, Seattle, WA.
Biter, William J. et al., "Magnetic Wire for Monitoring Strain in Composites", *Sensors*, Jun. 2001, www.sensormag.com, pp. 110-114.
Kanagaratnam, Prapa et. al., "Experience of robotic catheter ablation in humans using novel remotely steerable catheter sheath", Journal of Interventional Cardiac Electrophysiology. vol. 21, No. 1, p. 19-26 (2008).
Okumura, M.D. Yasuo et al. "A Systematic Analysis of *In Vivo* Contact Forces on Virtual Catheter Tip/Tissue Surface Contact during Cardiac Mapping and Intervention", Journal of Cardiovascular Electrophysiology, Jun. 2008, pp. 632-640, vol. 19, No. 6.
Partial European Search Report mailed on Sep. 18, 2009 from related European Patent Application No. 08253265.6.
Partial European Search Report mailed on Dec. 7, 2009 from related European Patent Application No. 09251502.2.
European Search Report mailed on Mar. 8, 2010 from related European Patent Application No. 09252143.4.
Partial European Search Report mailed on Mar. 29, 2010 from related European Patent Application No. 09252879.3.
Partial European Search Report mailed on Apr. 1, 2010 from related European Patent Application No. 09252721.7.

(56) References Cited

OTHER PUBLICATIONS

European Search Report mailed on Mar. 2, 2011 from related European Patent Application No. 10175931.4.
European Search Report mailed on Mar. 28, 2011 from related European Patent Application No. 10252189.5.
European Search Report mailed on Mar. 30, 2011 from related European Patent Application No. 10252020.2.
European Search Report mailed on May 16, 2011 from related European Patent Application No. 10252232.3.
European Search Report mailed on Aug. 5, 2011 from related European Patent Application No. 11158804.2.
European Search Report mailed on Sep. 20, 2011 from related European Patent Application No. 11250066.5.
European Search Report mailed on Oct. 28, 2011 from related European Patent Application No. 11171842.5.
European Search Report mailed on Nov. 17, 2011 from related European Patent Application No. 11177600.1.
European Search Report mailed on Feb. 15, 2012 from corresponding European Patent Application No. 11182854.7.
European Search Report mailed on May 2, 2012 from related European Patent Application No. 11189326.9.
European Search Report mailed on Jun. 4, 2012 from related European Patent Application No. 12163784.7.
European Search Report mailed on Jul. 20, 2012 from related European Patent Application No. 12161784.9.
European Search Report mailed on Nov. 20, 2012 from related European Patent Application No. 12176163.9.
European Search Report mailed on Feb. 11, 2013 from related European Patent Application No. 11187525.8.
European Search Report mailed on Apr. 9, 2013 from related European Patent Application No. 13150145.4.

* cited by examiner

US 8,731,859 B2

CALIBRATION SYSTEM FOR A FORCE-SENSING CATHETER

FIELD OF THE INVENTION

The present invention relates generally to invasive probes, and specifically to calibrating force sensors in invasive probes.

BACKGROUND OF THE INVENTION

A wide range of medical procedures involve placing objects, such as sensors, tubes, catheters, dispensing devices and implants, within a patient's body. Position sensing systems have been developed for tracking such objects. Magnetic position sensing is one of the methods known in the art. In magnetic position sensing, magnetic field generators are typically placed at known positions external to the patient. A magnetic field sensor within the distal end of a probe generates electrical signals in response to these magnetic fields, which are processed in order to determine the position coordinates of the distal end of the probe. These methods and systems are described in U.S. Pat. Nos. 5,391,199, 6,690,963, 6,484,118, 6,239,724, 6,618,612 and 6,332,089, in PCT International Publication WO 1996/005768, and in U.S. Patent Application Publications 2002/0065455 A1, 2003/0120150 A1 and 2004/0068178 A1, whose disclosures are all incorporated herein by reference.

When placing a probe within the body, it may be desirable to have the distal tip of the probe in direct contact with body tissue. The contact can be verified, for example, by measuring the contact pressure between the distal tip and the body tissue. U.S. Patent Application Publications 2007/0100332 and 2009/0093806, whose disclosures are incorporated herein by reference, describe methods of sensing contact pressure between the distal tip of a catheter and tissue in a body cavity using a force sensor embedded in the catheter.

SUMMARY OF THE INVENTION

An embodiment of the present invention provides apparatus, including:

a rolling element, which is resting on a surface;

a force-sensing device, which is coupled to the surface and is configured to make a first measurement indicative of a force exerted in a direction perpendicular to the surface by a force-sensing probe pressing against the rolling element so as to hold the rolling element stationary; and a calibration processor, which is configured to collect the first measurement from the sensing device, to collect a second measurement indicative of the force from the force-sensing probe, and to calibrate the force-sensing probe based on the first and second measurements.

Typically, the surface is planar.

In a disclosed embodiment the rolling element may be a silicone rubber ball.

Typically, the force-sensing device includes a load cell.

The processor may be configured to make the first measurement by collecting, from the force-sensing device, first signals indicating the force.

In an alternative embodiment the probe includes a flexible insertion tube, a distal tip, and a joint connecting a distal end of the flexible insertion tube to the distal tip. Typically, pressing the force-sensing probe against the rolling element causes a distortion of the distal tip. The processor may be configured to make the second measurement by reading from the probe one or more signals indicative of the distortion.

The distortion may consist of an axial displacement of the distal tip parallel to an axis of symmetry of the distal end. Alternatively or additionally, the distortion may consist of an angular deflection of the distal tip from an axis of symmetry of the distal end.

Typically, calibrating the probe includes computing one or more calibration coefficients for assessing the force as a function of the first and the second measurements. The processor may be configured to store the calibration coefficients to a memory coupled to the probe. The memory may include an Electronically Erasable Programmable Read Only Memory ($E^2$PROM).

There is further provided, according to an embodiment of the present invention, a method, including:

positioning a rolling element on a surface coupled to a force-sensing device;

pressing a force-sensing probe against the rolling element so as to hold the rolling element stationary on the surface while exerting, through the rolling element, a force on the force-sensing device in a direction perpendicular to the surface;

while pressing the force-sensing probe, making first and second measurements of the force using the force-sensing device and the probe, respectively; and calibrating the force-sensing probe based on the first and second measurements.

BRIEF DESCRIPTION OF THE DRAWINGS

The disclosure is herein described, by way of example only, with reference to the accompanying drawings, wherein.

DETAILED DESCRIPTION OF EMBODIMENTS

Some invasive probes, such as a catheter, comprise a force sensor for measuring a force between the catheter and intra-body tissue. For example, the force sensor is in a distal tip of the probe, and the tip distorts in response to a force exerted by the distal tip on endocardial tissue. The distortion of the distal tip provides an indication of the contact force. In many practical cases, however, the relationship between the actual contact force and measurements of the distortion varies from one catheter to another.

In order to ensure accurate force measurements, embodiments of the present invention provide methods and systems for calibrating probes (e.g., catheters) fitted with force sensors. In some embodiments, a calibration apparatus comprises a flexible, resilient rolling element, such as a silicone rubber ball, resting on a planar horizontal surface coupled to a sensing device.

During a calibration procedure, the distal tip of a force-sensing catheter is pressed against the ball at a given angle, which may cause the ball to roll. The ball rolls because the force applied by the distal tip against the ball creates both a torque (which causes the ball to roll), and a downward (i.e., vertical) force. If the ball does not roll (or when the ball stops rolling after changing the angle of engagement between the catheter and the ball), all the force applied by the distal tip to the ball is directed as a downward force which can be measured by the sensing device.

Pressing the distal tip against the ball may also cause the distal tip to distort in response to a force between the distal tip and the ball. When the distal tip distorts, a force sensor in the catheter produces distortion measurements of the distal tip. In some embodiments, a calibration processor receives the distortion measurements from the force sensor and the force measurements from the sensing device when the force applied by the distal tip to the ball is redirected as a downward force (i.e., when the ball is stationary). In this case, the calibration processor may compute calibration coefficients for assessing the force exerted by the catheter as a function of the distortion. Embodiments of the present invention provide a simple, inexpensive way to perform accurate calibration of the force sensor over multiple angles of contact with tissue.

In some embodiments, the calibration coefficients are stored in a non-volatile memory that is coupled to the catheter. When the catheter is later used in a medical system, the actual force exerted by the catheter's distal tip on the body tissue can be derived with high accuracy from the distortion measurements, using the calibration coefficients computed during the calibration procedure.

System Description

Figure 1:
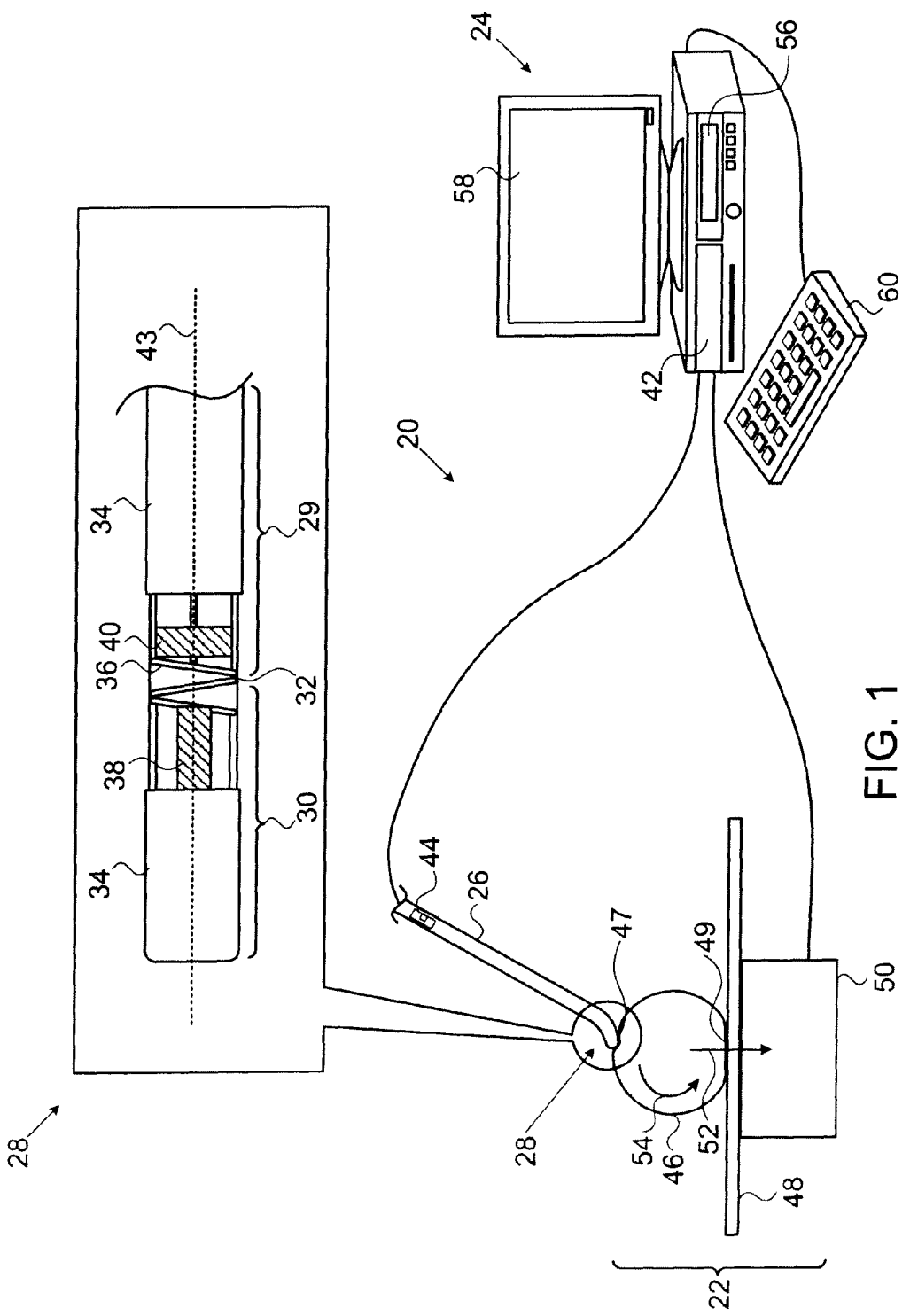
FIG. 1 is a schematic pictorial illustration of a calibration system for a force-sensing catheter, in accordance with an embodiment of the present invention.

FIG. 1 is an illustration of a calibration system 20 for a force-sensing catheter, in accordance with an embodiment of the present invention. System 20 comprises a calibration apparatus 22 coupled to a calibration unit 24. In the embodiment described hereinbelow, system 20 is used for calibrating a probe 26, which in the present example comprises a catheter used for therapeutic and/or diagnostic purposes in a heart or in other body organs.

Probe 26 comprises a distal end 28 for insertion into a body cavity of a patient during a medical procedure. Distal end 28 comprises a flexible insertion tube 29 connected to a distal tip 30 via a joint 32. The distal end of insertion tube 29 is covered by a flexible, insulating material 34. The area of joint 32 is covered, as well, by a flexible, insulating material, which may be the same as material 34 or may be specially adapted to permit unimpeded bending and compression of the joint. Material 34 is shown cut away in FIG. 1 in order to expose the internal structure of the catheter. Distal tip 30 is typically relatively rigid, by comparison with flexible insertion tube 29.

Distal tip 30 is connected to flexible insertion tube 29 by a resilient member 36. In FIG. 1, the resilient member has the form of a coil spring, but other types of resilient components may alternatively be used for this purpose. Resilient member 36 permits a limited range of relative movement between tip 30 and the distal end of flexible insertion tube 29 in response to forces exerted on the distal tip.

Distal tip 30 contains a magnetic position sensor 38. Sensor 38 may comprise one or more miniature coils, and typically comprises multiple coils oriented along different axes. (Sensor 38 is typically used to track the position of tip 30 during a medical procedure, by measuring magnetic fields generated by external generators.) The distal end of flexible insertion tube 29 contains a miniature magnetic field generator 40 near resilient member 36. Typically, field generator 40 comprises a coil, which is driven by a current conveyed through the catheter from calibration unit 24. Typically, the field generator is driven so that its magnetic field is distinguishable in time and/or frequency from the fields of the external generators operative during a medical procedure. Alternatively, position sensor 38 may comprise either another type of magnetic sensor, an electrode which serves as a position transducer, or position transducers of other types, such as impedance-based or ultrasonic position sensors. Although FIG. 1 shows a probe with a single position sensor, embodiments of the present invention may utilize probes with more than one position sensor.

The magnetic field created by field generator 40 causes the coils in sensor 38 to generate electrical signals at the drive frequency of the field generator. The amplitudes of these signals will vary depending upon the location and orientation of distal tip 30 relative to the distal end of flexible insertion tube 29. A calibration processor 42 in calibration unit 24 processes these signals in order to determine the axial displacement, i.e., lateral movement along or parallel to an axis 43 of the catheter, and the magnitude of the angular deflection of the distal tip from the catheter axis. Axis 43 is an axis of symmetry of the distal end of flexible insertion tube 29. The displacement and the deflection of distal tip 30 are collectively referred to herein as a distortion of the distal tip. (Because of the axial symmetry of the field generated by a coil, only the magnitude of the deflection can be detected using a single coil in field generator 40, and not the direction of the deflection. Optionally, field generator 40 may comprise two or more coils, in which case the direction of deflection may be determined, as well.) The magnitudes of the displacement and deflection may be combined by vector addition to give a total magnitude of the movement of distal tip 30 relative to the distal end of flexible insertion tube 29.

The movement of distal tip 30 relative to the distal end of flexible insertion tube 29 gives a measure of the distortion of resilient member 36. Thus, the combination of field generator 40 with sensor 38 serves as a force sensing system. By virtue of the combined sensing of displacement and deflection, and after the calibration described herein, this force sensing system gives a correct measure of the force regardless of whether the force is exerted on distal tip 30 head-on or at an angle. Further details of this sort of probe and position sensor are described in U.S. Patent Application Publications 2009/0093806 and 2009/0138007, cited above.

Probe 26 also comprises a non-volatile memory 44, such as electronically erasable programmable read only memory ($E^2PROM$), which is configured to store calculation coefficients computed during calibration. As discussed supra, when the catheter is later used in a medical system, the actual force exerted by the catheter's distal tip on body tissue can be derived with high accuracy from the displacement and the deflection measurements, using the calibration coefficients stored in memory 44.

Calibration apparatus 22 comprises a silicone rubber ball 46 and a surface 48. Surface 48 is assumed, by way of example, to be planar and horizontal. In the embodiment of FIG. 1, ball 46 can freely roll on surface 48 when distal tip 30 is pressed against the ball. In some embodiments, distal tip 30 pressing against ball 46 may create an indentation 47 where the distal tip presses against the ball, and/or a deformation 49 (i.e., a flattening) where the ball presses against planar surface 48.

In addition to ball 46 and surface 48, calibration apparatus 22 comprises a load cell 50 coupled to the planar surface. The load cell measures a downward force 52 exerted by the distal tip on surface 48, and generates electrical signals indicating the downward force. Additionally, there may be a torque 54 when distal tip 30 is pressed against ball 46, which causes the ball to roll on surface 48. Although the system shown in FIG. 1 measures the downward force using load cell 50, system 20 may use any other suitable type of sensor to measure the downward force, and such sensors are thus considered to be within the spirit and scope of this invention.

Both load cell 50 and probe 26 are connected to calibration unit 24 via suitable interfaces (e.g., cables and connectors). Calibration unit 24 comprises calibration processor 42, a memory 56, a display 58 and an input device 60, such as a keyboard. Processor 42 typically comprises a general-purpose computer, with suitable front end and interface circuits for receiving signals from position sensor 38 and load cell 50, as well as for controlling the other components of calibration unit 24. Processor 42 may be programmed in software to carry out the functions that are described herein. The software may be downloaded to processor 42 in electronic form, over a network, for example, or it may be provided on non-transitory tangible media, such as optical, magnetic or electronic memory media. Alternatively, some or all of the functions of processor 42 may be carried out by dedicated or programmable digital hardware components.

Catheter Calibration Using a Single Axis Load Cell

Figure 2:
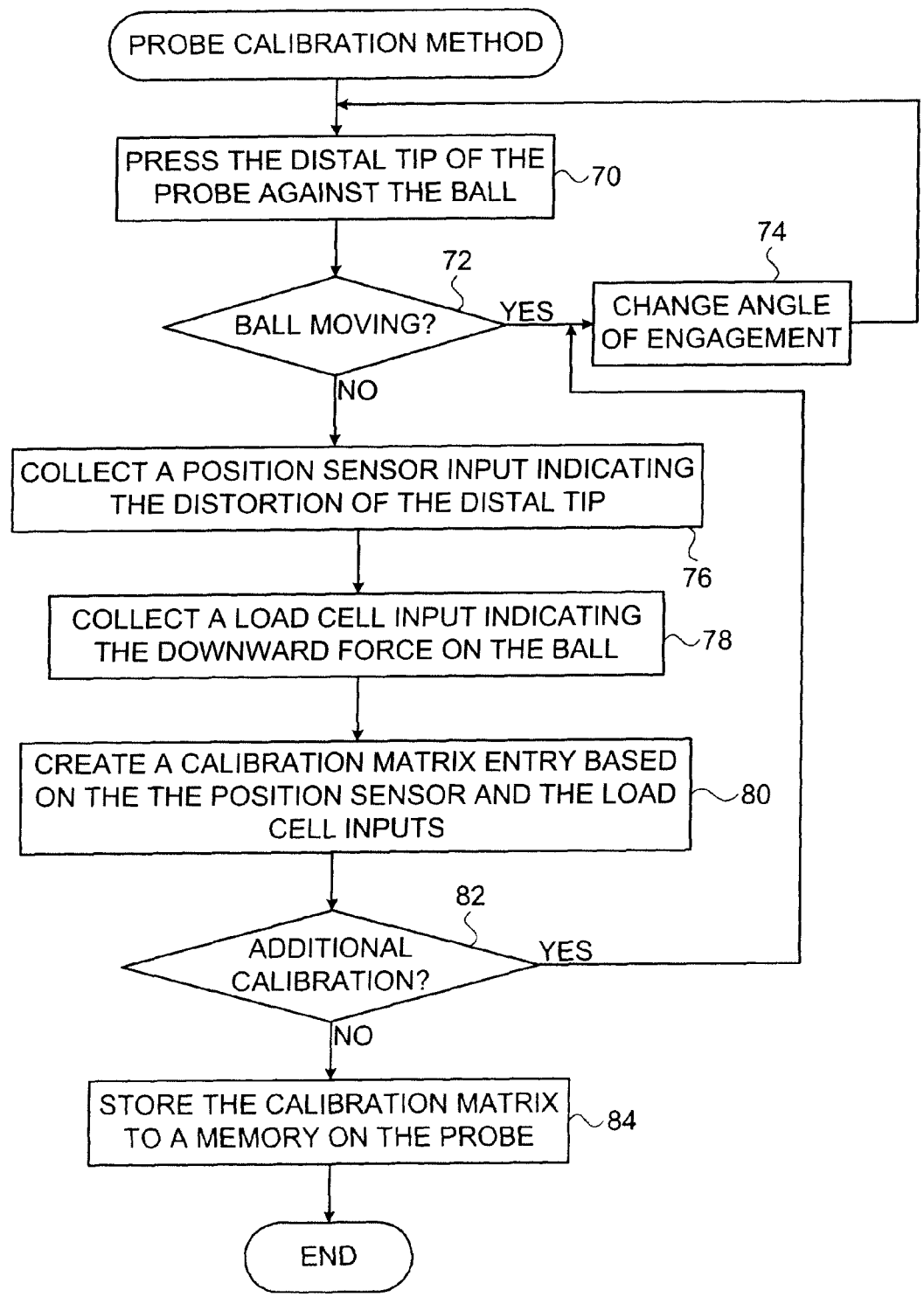
FIG. 2 is a flow diagram that schematically illustrates a method of calibrating the force-sensing catheter, in accordance with an embodiment of the present invention.

FIG. 2 is a flow diagram that schematically illustrates a method of calibrating a force-sensing catheter, in accordance with an embodiment of the present invention. In an initial step 70, an operator (not shown) presses distal tip 30 against ball 46. Pressing distal tip 30 against ball 46 causes catheter 26 to bend at joint 32, thereby distorting the distal tip. Position sensor 38 in distal tip 30 outputs a signal indicative of the distortion, i.e., the displacement and the deflection, of the distal tip. Simultaneously, load cell 50 outputs a measurement indicative of the downward force exerted by distal tip 30 on ball 46. Both the distortion and the downward force measurements are transmitted to calibration unit 24. Note that prior to the calibration procedure, the operator typically zeroes load cell 50 (via keyboard 60) in order to account for the weight of the ball.

Pressing distal tip 30 against ball 46 may also deform the ball slightly (e.g., indentation 47 and/or deformation 49). Any large enough torque 54 caused by distal tip 30 pressing against ball 46 may cause the ball to roll. In a first comparison step 72, if ball 46 is moving, i.e., is rolling, then in a repositioning step 74, the operator changes the angle of engagement between probe 26 and the ball, and the method returns to step 70. Returning to step 72, if ball 46 is stationary, i.e., is not rolling, then distal tip 30 is exerting only downward force 52 (i.e., in a direction perpendicular to surface 48) towards the ball, thereby holding the ball stationary. When ball 46 is stationary, the downward force measured by load cell 50 equals the force between the distal tip and the ball.

While distal tip 30 presses against ball 46, calibration unit 24 collects, in a first collection step 76, a first signal from sensor 38 indicating distortion measurements. Calibration unit 24 also collects, in a second collection step 78, a second signal from load cell 50 indicating the downward force measurements.

In a calibration step 80, processor 42 computes calibration coefficients using the collected distortion and downward force measurements. By mapping the distortion measurements from position sensor 38 against the force measurements from load cell 50, the calibration coefficient determines the force on distal tip 30 based on the position sensor measurements, thereby calibrating probe 26. In other words, a given calibration coefficient, e.g., comprising an ordered pair of numbers indicating deflection and displacement measurements, translates the distortion measurement of tip 30 into an actual force reading.

In a second comparison step 82, if additional calibration is desired, then the method returns to step 74 above. Otherwise, in a storing step 84, processor 42 stores the calibration matrix to memory 44 on the probe, and the method terminates.

To store the calibration matrix, processor 42 may store an analytic calculation to memory 44 based on the computed coefficients. Alternatively, processor 42 may store a lookup table with inter-measurement interpolation to memory 44.

Figure 3:
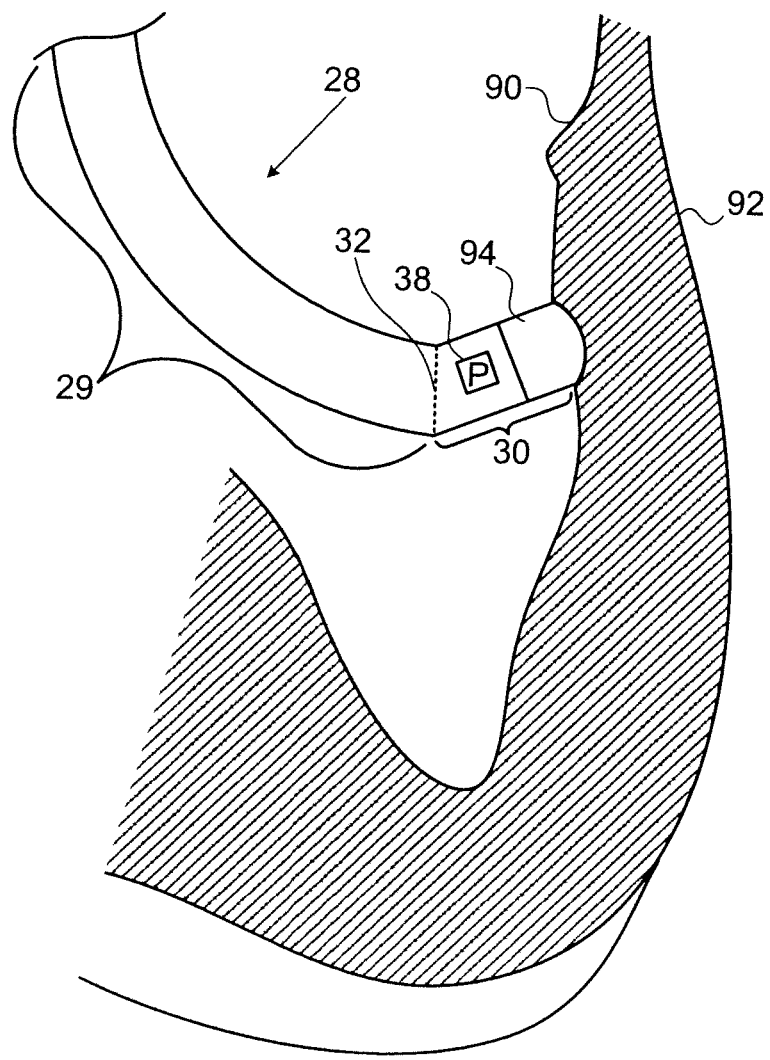
FIG. 3 is a schematic detail view showing a distal tip of the force-sensing catheter in contact with endocardial tissue, in accordance with an embodiment of the present invention.

FIG. 3 is a schematic detail view showing distal tip 30 in contact with an endocardial tissue 90 of a heart 92, in accordance with an embodiment of the present invention. In the present example, tip 30 comprises an electrode 94. In some electrophysiological diagnostic and therapeutic procedures, such as intracardiac electrical mapping, it is important to maintain the proper level of force between electrode 94 and tissue 90. As a medical professional (not shown) presses distal tip 30 against endocardial tissue 90, the catheter bends at joint 32. Sufficient force is needed in order to ensure good electrode contact between the distal tip and the tissue. Poor electrical contact can result in inaccurate readings. On the other hand, excessive force can deform the tissue and thus distort the map.

When distal tip 30 presses against tissue 90, sensor 38 produces measurements that are indicative of the distortion of tip 30 with respect to the distal end of flexible insertion tube 29. The medical imaging system (e.g., a mapping system—not shown) translates these measurements into accurate force readings using the calibration coefficients stored in memory 44 of the probe. Thus, calibration of the invasive probe using embodiments of the present invention ensures that the medical professional can accurately control the force exerted by the probe on the tissue.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An apparatus, comprising:
   a rolling element, which is resting on a surface;
   a force-sensing device, which is coupled to the surface and is configured to make a first measurement indicative of a force exerted in a direction perpendicular to the surface by a force-sensing probe pressing against the rolling element so as to hold the rolling element stationary; and
   a calibration processor, which is configured to collect the first measurement from the sensing device, to collect a second measurement indicative of the force from the force-sensing probe, and to calibrate the force-sensing probe based on the first and second measurements.

2. The apparatus according to claim 1, wherein the surface is planar.

3. The apparatus according to claim 1, wherein the rolling element comprises a silicone rubber ball.

4. The apparatus according to claim 1, wherein the force-sensing device comprises a load cell.

5. The apparatus according to claim 1, wherein the processor is configured to make the first measurement by collecting, from the force-sensing device, first signals indicating the force.

6. The apparatus according to claim 1, wherein the probe comprises a flexible insertion tube, a distal tip, and a joint connecting a distal end of the flexible insertion tube to the distal tip.

7. The apparatus according to claim 6, wherein pressing the force-sensing probe against the rolling element causes a distortion of the distal tip.

8. The apparatus according to claim 7, wherein the processor is configured to make the second measurement by reading from the probe one or more signals indicative of the distortion.

9. The apparatus according to claim 7, wherein the distortion comprises an axial displacement of the distal tip parallel to an axis of symmetry of the distal end.

10. The apparatus according to claim 7, wherein the distortion comprises an angular deflection of the distal tip from an axis of symmetry of the distal end.

11. The apparatus according to claim 1, wherein calibrating the probe comprises computing one or more calibration coefficients for assessing the force as a function of the first and the second measurements.

12. The apparatus according to claim 11, wherein the processor is configured to store the calibration coefficients to a memory coupled to the probe.

13. The apparatus according to claim 12, wherein the memory comprises an Electronically Erasable Programmable Read Only Memory ($E^2$PROM).

14. A method, comprising:
positioning a rolling element on a surface coupled to a force-sensing device;
pressing a force-sensing probe against the rolling element so as to hold the rolling element stationary on the surface while exerting, through the rolling element, a force on the force-sensing device in a direction perpendicular to the surface;
while pressing the force-sensing probe, making first and second measurements of the force using the force-sensing device and the probe, respectively; and
calibrating the force-sensing probe based on the first and second measurements.

15. The method according to claim 14, wherein the surface is planar.

16. The method according to claim 14, wherein the rolling element comprises a silicone rubber ball.

17. The method according to claim 14, wherein the force-sensing device comprises a load cell.

18. The method according to claim 14, wherein making the first measurement comprises collecting, from the force-sensing device, first signals indicating the exerted force.

19. The method according to claim 14, wherein the probe comprises a flexible insertion tube, a distal tip, and a joint connecting a distal end of the flexible insertion tube to the distal tip.

20. The method according to claim 19, wherein pressing the force-sensing probe against the rolling element causes a distortion of the distal tip.

21. The method according to claim 20, wherein making the second measurement comprises reading from the probe one or more signals indicative of the distortion.

22. The method according to claim 20, wherein the distortion comprises an axial displacement of the distal tip parallel to an axis of symmetry of the distal end.

23. The method according to claim 20, wherein the distortion comprises an angular deflection of the distal tip from an axis of symmetry of the distal end.

24. The method according to claim 14, wherein calibrating the probe comprises computing one or more calibration coefficients for assessing the force as a function of the first and the second measurements.

25. The method according to claim 24, and comprising storing the calibration coefficients to a memory coupled to the probe.

26. The method according to claim 25, wherein the memory comprises an Electronically Erasable Programmable Read Only Memory ($E^2$PROM).

* * * * *